United States Patent
Lin et al.

(10) Patent No.: US 7,377,934 B2
(45) Date of Patent: May 27, 2008

(54) DEVICE AND SYSTEM FOR ANCHORING TISSUE TO BONE

(75) Inventors: Chih-I Lin, Pasadena, CA (US);
Kwan-Ku Lin, Pasadena, CA (US)

(73) Assignee: A-Spine Holding Group Corp., Road Town, Tortola (VG)

( * ) Notice: Subject to any disclaimer, the term of this patent is extended or adjusted under 35 U.S.C. 154(b) by 269 days.

(21) Appl. No.: 11/295,659

(22) Filed: Dec. 7, 2005

(65) Prior Publication Data

US 2006/0149260 A1  Jul. 6, 2006

Related U.S. Application Data

(63) Continuation of application No. 10/611,997, filed on Jul. 3, 2003, now abandoned.

(30) Foreign Application Priority Data

Apr. 30, 2003  (TW) ................ 92110213 A (51) Int. Cl.
*A61B 17/04* (2006.01)

(52) U.S. Cl. ............... 606/232; 606/60; 606/63; 606/72

(58) Field of Classification Search ............ 606/60, 606/61, 62, 63, 72, 232, 233
See application file for complete search history.

(56) References Cited

U.S. PATENT DOCUMENTS

| 5,439,476 | A | 8/1995 | Frantzides | 606/192 |
| 5,549,679 | A | 8/1996 | Kuslich | 623/17.12 |
| 6,712,851 | B1 * | 3/2004 | Lemperle et al. | 623/16.11 |
| 6,827,743 | B2 | 12/2004 | Eisermann et al. | 623/23.54 |
| 6,869,445 | B1 * | 3/2005 | Johnson | 623/17.11 |
| 2002/0026195 | A1 * | 2/2002 | Layne et al. | 606/72 |

* cited by examiner

*Primary Examiner*—Michael J. Hayes
*Assistant Examiner*—Michael G. Mendoza
(74) *Attorney, Agent, or Firm*—Bacon & Thomas, PLLC (57) ABSTRACT

A device is designed to anchor a tissue to a bone. The device comprises a contractible implant, one or more sutures attached to the implant, and a pasty medicine capable of solidification. The implant is made of a flexible wall and provided with a holding portion and an injection port. The flexible wall is provided with a plurality of pores, each having a diameter smaller than 0.1 millimeter. The pasty medicine is injected into the holding portion of the implant upon completion of insertion of the contracted implant into the bone, thereby resulting in expansion of the contracted implant. The implant is thus securely lodged in the bone upon solidification of the pasty medicine to facilitate the anchoring of the tissue to the bone by suturing.

15 Claims, 9 Drawing Sheets

DEVICE AND SYSTEM FOR ANCHORING TISSUE TO BONE

This application is a continuation application of pending U.S. application Ser. No. 10/611,997, filed Jul. 3, 2003 (of which the entire disclosure of the pending, prior application is hereby incorporated by reference).

FIELD OF THE INVENTION

The present invention relates generally to a surgical method of joining together a bone and a tissue, and more particularly to an anchoring device by which a tissue is firmly held on to a bone.

BACKGROUND OF THE INVENTION

The U.S. Pat. No. 6,007,566 discloses a system for anchoring tissue to bone. The system comprises an anchorlike implant which is provided with two flukes opposite to each other. The implant is fixed with a bone by means of the two flukes. The anchorlike implant of the prior art system often fails to bring about a good anchoring effect. In other words, the anchorlike implant is vulnerable to being pulled out of the bone in which it is implanted, due to the fact that the pointed flukes are apt to penetrate the bone at the time when the flukes are exerted on by a stress. The stress is bound to concentrate at the pointed end of the flukes of the anchorlike implant as the suturing threads are pulled by the tissue.

SUMMARY OF THE INVENTION

It is the primary objective of the present invention to provide a device for anchoring a tissue to a bone. The device comprises an implant, one or more sutures, and a pasty medicine.

The implant of the device is contractibe prior to being implanted in a bone. Upon completion of being implanted in the bone, the implant is filled with the pasty medicine and is therefore caused to expand to lodge in the bone. With the sutures, one or more pieces of the tissue are anchored to the bone. The sutures are fastened at one end with the implant such that other end of the sutures is extended out of the bone so as to join with the tissue pieces.

A device for anchoring a tissue to a bone according to one aspect of the present invention comprises:

an implant made of a flexible wall and provided with a holding portion and an injection port in communication with said holding portion, with said holding portion being enclosed by said flexible wall which is provided with a plurality of pores, each having a diameter smaller than 0.1 mm whereby said implant is contractible and is contracted prior to being inserted into the bone;

one or more sutures fastened with said implant; and a pasty medicine capable of solidification injected into said holding portion via said injection port of said implant in the wake of insertion of said implant into the bone, thereby resulting in expansion of said implant so as to enable said implant to be securely lodged in the bone upon completion of the solidification of said pasty medicine.

Preferably, said flexible wall of said implant is of a one-layered construction.

Preferably, said flexible wall of said implant is of a laminated multi-layered construction.

Preferably, said sutures are fastened at one end with said implant.

Preferably, said injection port of said implant is provided with a suture hole for holding said sutures.

Preferably, said implant is integrally made of said flexible wall such that said implant takes the form of sac, bag, or ball.

Preferably, said pasty medicine is a mixture of a liquid and a bone cement. More preferably, said bone cement is selected from the group consisting of gypsum, calcium sulfate, calcium phosphate, poly(methylmethacrylate) and hydroxy apatite.

It is another objective of the present invention to provide a system by which a tissue is anchored to a bone in a surgical operation.

The system of the present invention comprises said implant, said one or more sutures, an injection tool, and said pasty medicine, wherein said injection tool is fastened detachably with said filling member, so that said pasty medicine is injected into said holding portion via said injection tool.

Preferably, said injection tool comprises a connection tube and a syringe formed of a barrel and a plunger, said connection tube being fastened detachably at one end with said injection port of said filling member, said connection tube further being fastened at other end with said barrel of said syringe; wherein said pasty medicine is injected into said holding portion of said filling member from said barrel by said plunger via said connection tube.

Preferably, said system of the present invention further comprises a sleeve receiving said connection tube and said implant prior to insertion of said implant into the bone, wherein said sutures protrude from said sleeve. More preferably, said sleeve is made of a material having an elasticity and has a longitudinal slit, so that said sleeve can be removed from said connection tube by expanding said longitudinal slit.

The pores of the flexible wall of the implant of the present invention allow the bone cells to grow thereinto to help the implant serving as an anchor.

The flexible wall of the implant of the device or system of the present invention is made of a biocompatible or biosynthetic material, such as threads made of titanium or goat intestine.

The flexible wall of the implant of the device or system of the present invention further contains an image-forming body, which is formed of a metal conductor, or graphite. The image-forming body enables the implant to be located in the bone by a ray imaging system, such as an X-ray machine.

If the average diameter of the pores of the flexible wall of the implant of the device or system of the present invention is close to 0.1 mm, the flexible wall is preferably formed of two or more layers which are laminated. Generally speaking, if the particle size of the pasty medicine, such as poly (methylmethacrylate), is relatively large, and the pasty medicine has a high viscosity, the flexible wall can be formed of two layers. If the particle size of the pasty medicine is relatively small, and the pasty medicine has a low viscosity, the flexible wall is preferably formed of three or more layers. In another words, the number of the wall layer depends on the viscosity or particle size of the pasty medicine. If the flexible wall is of a multi-layered construction, the wall layers are laminated in such a manner that the pores of the wall layers are not necessarily corresponding in location to one another.

The flexible wall of the implant of the device or system of the present invention is provided with a thread hole dimensioned to allow passage of one end of the sutures. When the implant of the device or system of the present invention is formed of biocompatible or biosynthetic threads by knitting, the thread hole can be formed by knitting near the injection port of the implant. Alternatively, the sutures can be integrally knitted to the flexible wall of the implant without forming the thread hole.

This specification contains such words as "front", "rear", "left", and "right". The word "front" refers to a direction in which the device or system of the present invention is moved by a surgeon toward a subject under the surgical treatment. The word "rear" refers to the opposite direction of the "front". The word "left" refers to a direction in which the device or system of the present invention is moved by the surgeon toward the left arm of the surgeon. The word "right" refers to a direction toward the right arm of the surgeon.

The features and the advantages of the present invention will be more readily understood upon a thoughtful deliberation of the following detailed description of the preferred embodiments of the present invention with reference to the accompanying drawings.

DETAILED DESCRIPTION OF THE PREFERRED EMBODIMENTS

Figure 1A:
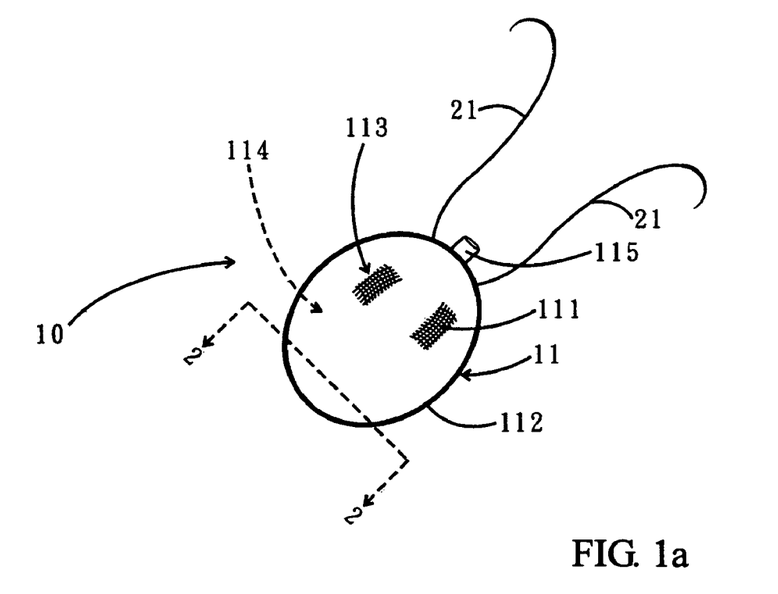
FIGS. 1a and 1b are perspective view of the implants and the surgical sutures of a first preferred embodiment of the present invention.

As shown in FIG. 1a, a device 10 made according to a first embodiment of the present invention is used to anchor a tissue to a bone. The device 10 comprises an implant 11 which is formed of a plurality of biocompatible or biosynthetic threads 111 by knitting. In the process of forming the implant 11, the threads 111 are first knitted into a flexible wall 112 along with one or more suturing threads 21. The implant 11 is in the form of a bag having a holding portion enclosed by the flexible wall 112. In light of the flexible wall 112 being formed by knitting, the flexible wall 112 is provided with a plurality of meshes (pores) 113, each having a diameter smaller than 0.1 mm.

The flexible wall 112 forming the holding portion 114 is folded or contracted at the top thereof to form an opening, and a ring having threads on its inner surface is fastened to the opening to form an injection port 115.

Figure 1B:
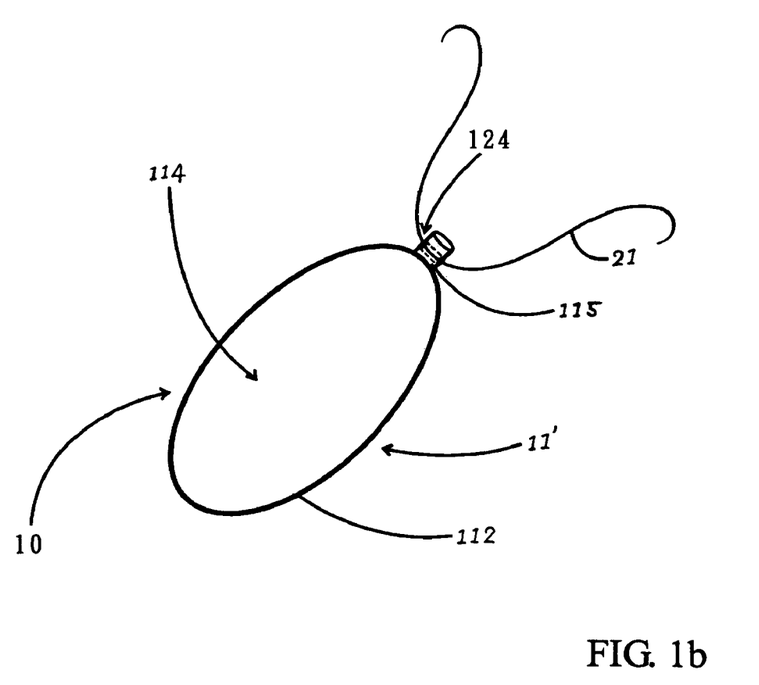

A device 10 made according to a second embodiment of the present invention comprises an implant 11' which is basically similar to the implant 11 described above, with the difference being that the implant 11' is provided at an injection port 115 thereof with a suture hole 124 for receiving one or more suturing threads 21. In another words, the suturing threads 22, the flexible wall 112 of the holding portion 114 of the implant 11' are not integrally formed.

Figure 2A:
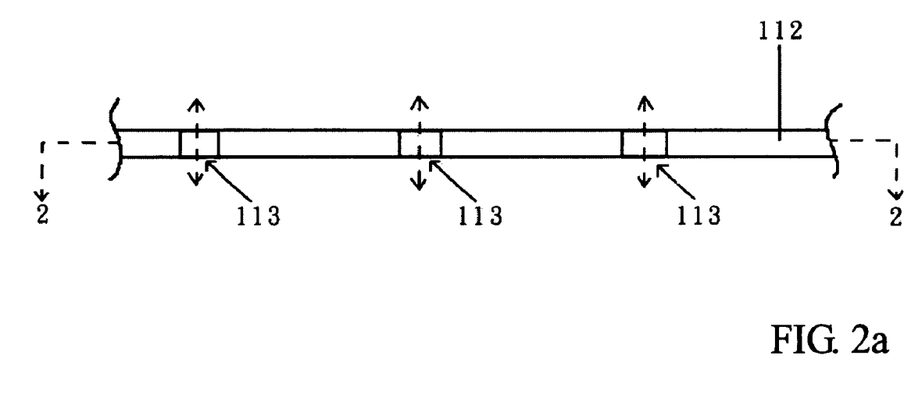
FIGS. 2a and 2b are sectional schematic view of a one-layered wall and a multi-layered wall of the first preferred embodiment of the present invention.
Figure 2B:
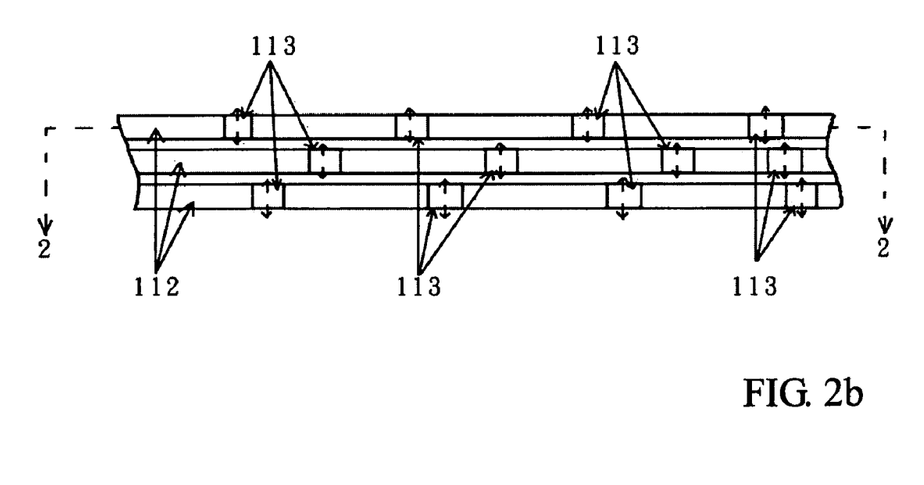

FIGS. 2a and 2b are two sectional views which are taken along a line 2-2 as shown in FIG. 1a. The flexible wall 112 is of a one-layered construction as shown in FIG. 2a, or a laminated multi-layered construction as shown in FIG. 2b. Each layer is provided with a plurality of pores 113 permeable to fluids. The layers are laminated in such a manner that the pores 113 of the layers are not corresponding in location to one another, as shown in FIG. 2b, thereby slowing down the passage of the fluids through the pores 113.

Figure 3:
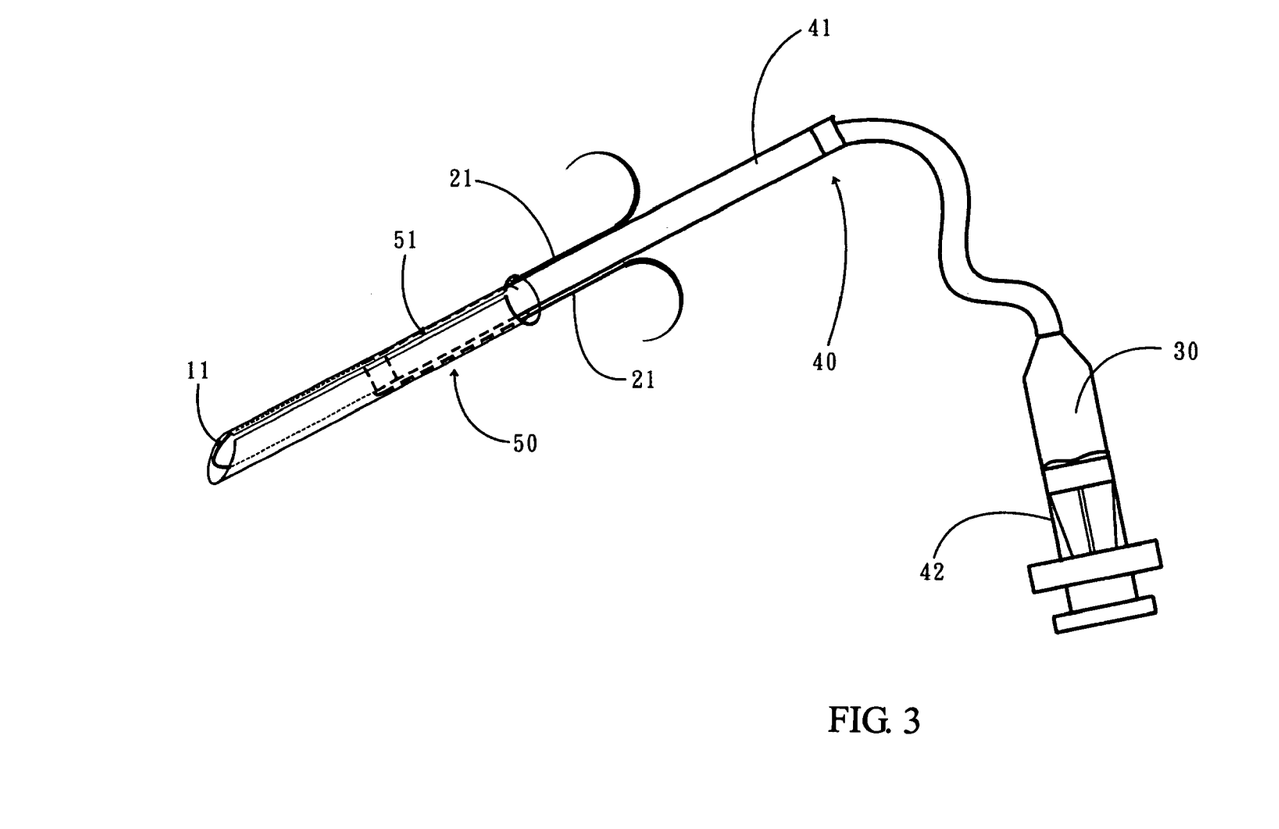
FIG. 3 shows a perspective view of a system embodied in the present invention.

As shown in FIG. 3, an anchoring system embodied in the present invention comprises the implant 11, two suturing threads 21 formed integrally with the implant 11, a pasty medicine 30, an implantation-injection tool 40, and a sleeve 50. The sleeve 50 is provided with a slit 51 extending along the longitudinal direction of the sleeve 50. The implantation-injection tool 40 comprises a connection tube 41 and a syringe 42.

Figure 4A:
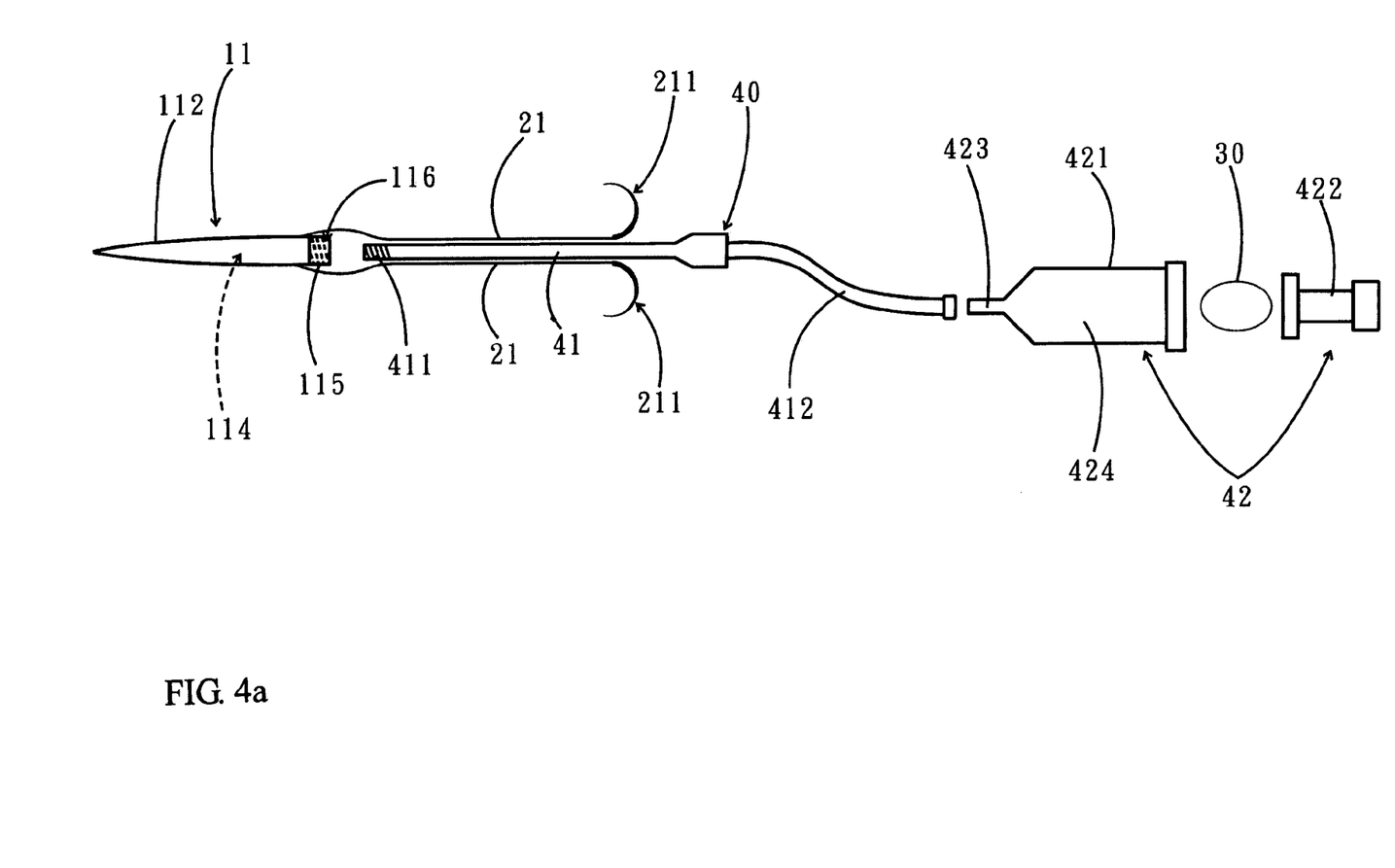
FIG. 4a shows an exploded view of the system is shown in FIG. 3.
Figure 4B:
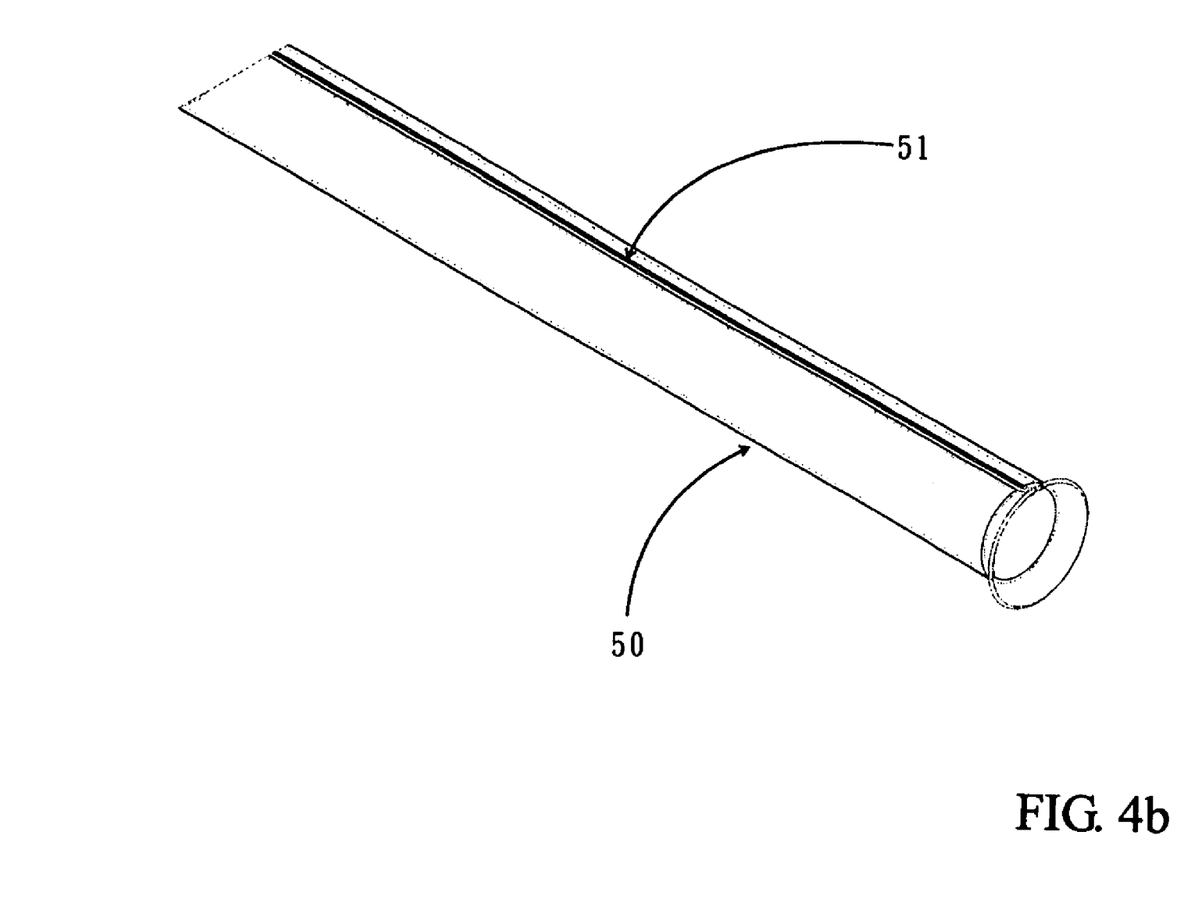
FIG. 4b shows a perspective view of a sleeve of the system as shown in FIG. 3.

As shown in FIGS. 4a and 4b, the implant 11 is formed of titanium threads or goat intestine threads such that it is contractible. The injection port 115 is provided with a plurality of inner threads 116. In the meantime, the connection tube 41 is provided at one end with a plurality of outer threads 411 engageable with the inner threads 116 of the injection port 115 of the implant 11.

Depending on the surgical requirement, one or two suturing threads 21 are integrally formed with the implant 11. The suturing threads 21 are provided with a surgical needle 211.

The pasty medicine 30 is capable of solidification. However, the pasty medicine 30 may be existed in the powdered or colloidal form; it is mixed with a liquid, such as water, to become the pasty substance, which is then injected into the implant by the injection tool 40. The pasty medicine 30 is contained in the receiving space 424 of the barrel 421 of the syringe 42. The barrel 421 has a connection end 423 which is connected with a hose 412 of the connection tube 41. The pasty medicine 30 is forced by the plunger 422 of the syringe 42 into the holding portion 114 of the implant 11 via the connection tube 41, thereby resulting in expansion of the implant 11. Upon being injected into the implant 11, the pasty medicine 30 begins to solidify.

The sleeve 50 is made of a material having an elasticity, such as titanium, stainless steel, plastic, etc. The sleeve 50 is used to fit around the contracted implant 11 and the connection tube 41 of the injection device 40, so as to facilitate the inserting of the contracted implant 11 into a bone tissue. The sleeve 50 is provided with a slit 51 extending along the longitudinal direction of the sleeve 50, as shown in FIG. 4b. In light of the sleeve 50 being elastic by nature, the slit 51 can be forced to widen to enable the sleeve 50 to be separated from the connection tube 41 via the slit 51.

Figure 5A:
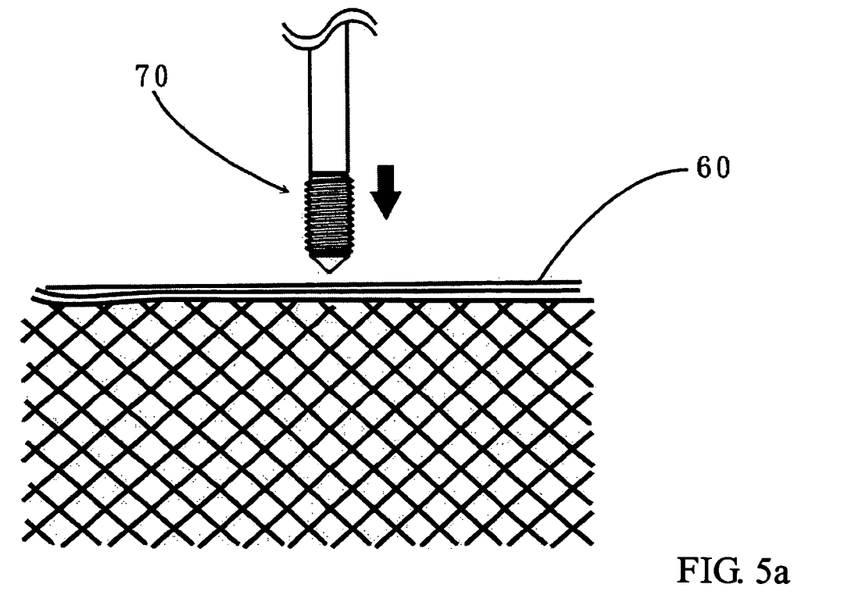
FIGS. 5a-5e are a series of schematic views of the system of the present invention at work.
Figure 5B:
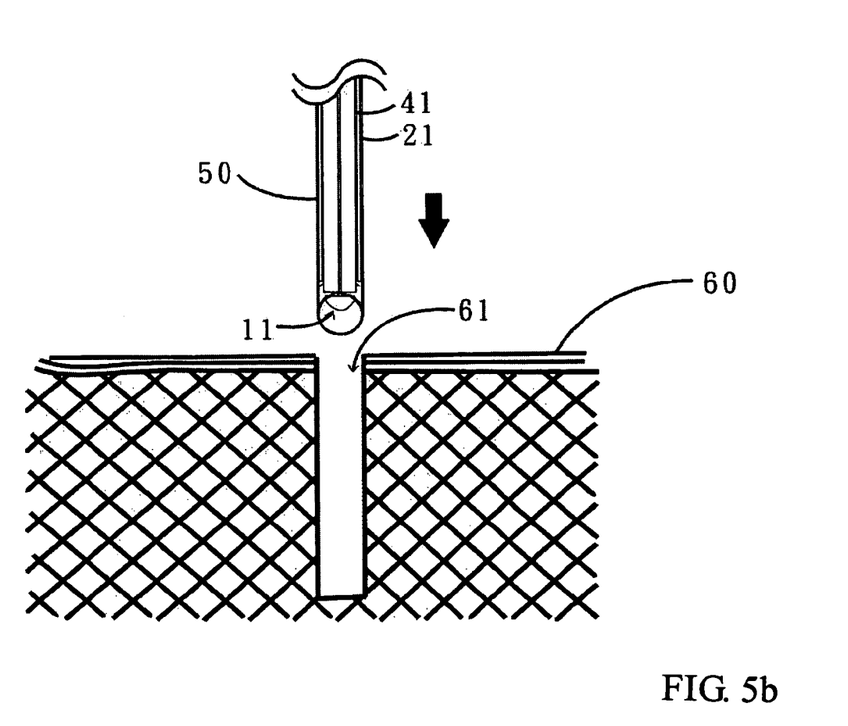
Figure 5C:
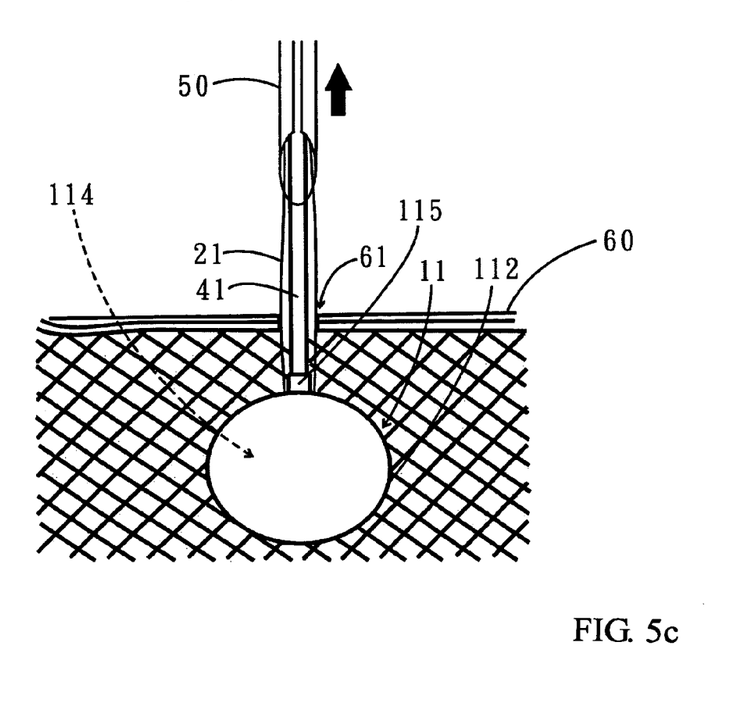

The surgical process of anchoring a soft tissue, such as muscular tissue, to a bone tissue is described hereinafter with reference to FIGS. 5a-5e. In the first place, a drilling tool 70 is used to make a hole 61 in a bone tissue 60, as illustrated in FIGS. 5a and 5b. Thereafter, the contracted implant 11, the suturing threads 21, and the connection tube 41 of the injection device 40 are fitted into the sleeve 50, which is then inserted into the hole 61 of the bone tissue 60. The sleeve 50 is withdrawn from the hole 61. The pasty medicine 30, which is held in the receiving space 424 of the barrel 421 of the syringe 42 of the injection device 40 (not shown in FIGS. 5a and 5b), is injected into the holding portion 114 of the implant 11, thereby resulting in expansion of the flexible wall 112 of the implant 11, as illustrated in FIG. 5c. As a result, the implant 11 is securely lodged in the bone tissue 60 upon solidification of the pasty medicine 30.

Figure 5D:
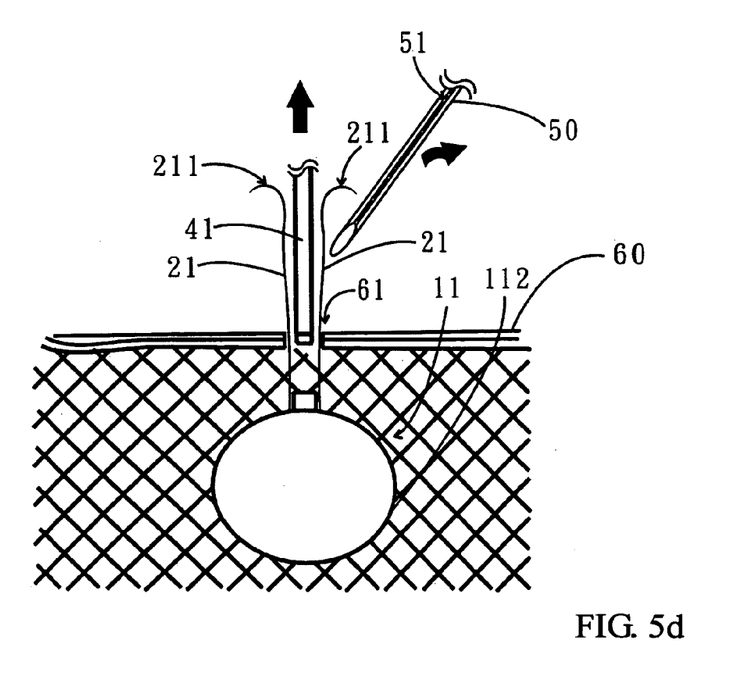
Figure 5E:
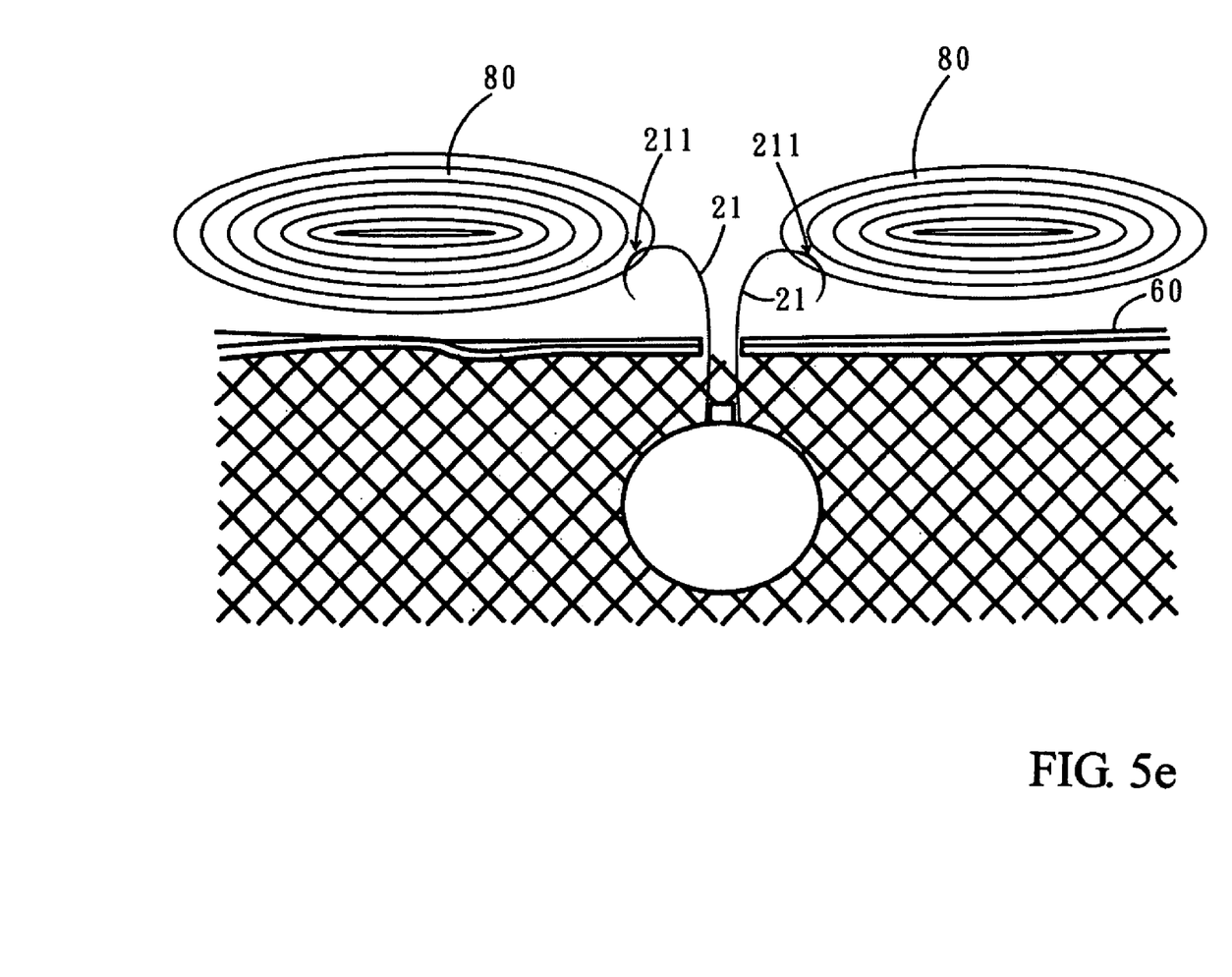

By widening the slit 51 of the sleeve 50, the sleeve 50 is separated from the connection tube 41 before the connection tube 41 is disconnected with the injection port 115 of the implant 11, as shown in FIG. 5d. Upon completion of the removal of the connection tube 41 and the sleeve 50, the anchorage of two muscular tissues 80 is carried out by suturing, as shown in FIG. 5e. With two surgical sutures 21 along with two suturing needles 211, the two muscular tissues 80 are anchored to the bone tissue 60.

Figure 6:
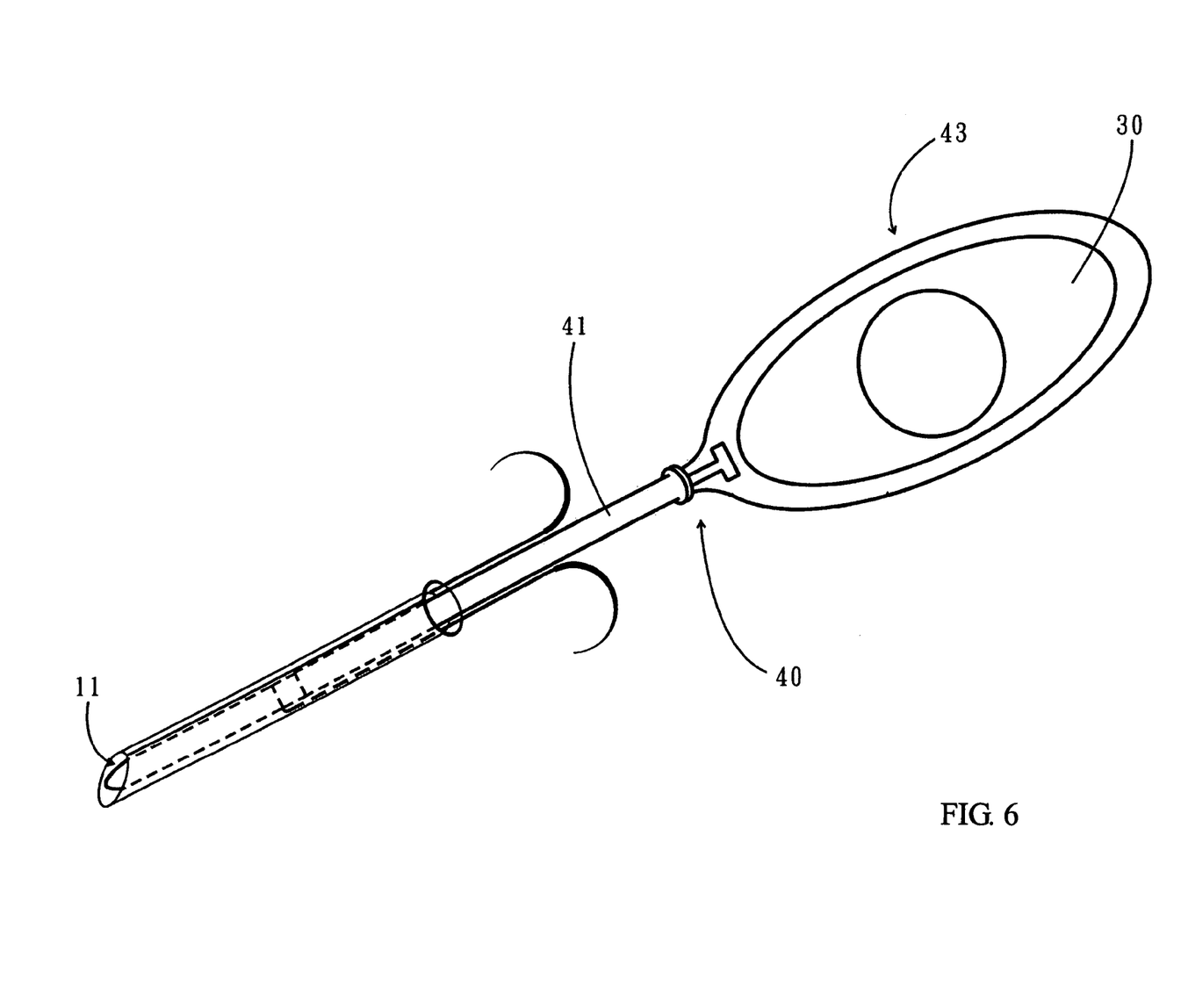
FIG. 6 shows a perspective view of an implantation-injection device of a second preferred embodiment of the present invention.

As shown in FIG. 6, the injection tool 40 of the system of the present invention further comprises a packaging sac 43 which is integrally formed with the connection tube 41. The packaging sac 43 is used to hold a medicine and a solution, which are thoroughly mixed to form the pasty medicine 30 before the injection of the medicine 30 into the contracted implant 11 takes place.

The embodiments of the present invention described above are to be regarded in all respects as being illustrative and nonrestrictive. Accordingly, the present invention may be embodied in other specific forms without deviating from the spirit thereof. The present invention is therefore to be limited only by the scopes of the following claims.

What is claimed is:

1. A method for anchoring a tissue to a bone, said method comprising the following steps:

inserting an implant into a bone, said implant made of a flexible wall and provided with a holding portion and an injection port in communication with said holding portion, with said holding portion being enclosed by said flexible wall which is provided with a plurality of pores, each having a diameter smaller than 0.1 mm, wherein said implant is contractible and is contracted prior to being inserted into the bone, wherein said implant is provided with one or more sutures, said sutures are fastened at one end with said implant, such that other end of the sutures is extended out of the bone;

injecting a pasty medicine capable of solidification into said holding portion via said injection port of said implant in the wake of insertion of said implant into the bone, thereby resulting in expansion of said implant so as to enable said implant to be securely lodged in the bone upon completion of the solidification of said pasty medicine; and fastening the other end of one or more sutures with a tissue.

2. The method as defined in claim 1, wherein said flexible wall of said implant is of a one-layered construction.

3. The method as defined in claim 1, wherein said flexible wall of said implant is of a laminated multi-layered construction.

4. The method as defined in claim 1, wherein said injection port of said implant is provided with a suture hole for holding said sutures.

5. The method as defined in claim 1, wherein said implant is integrally made of said flexible wall such that said implant takes the form of sac, bag, or ball.

6. The method as defined in claim 1, wherein said pasty medicine is a mixture of a liquid and a bone cement.

7. The method as defined in claim 6, wherein said bone cement is selected from the group consisting of gypsum, calcium sulfate, calcium phosphate, poly(methylmethacrylate) and hydroxy apatite.

8. The method as defined in claim 1, wherein said implant is provided with an imaging body of a metal conductor or graphite.

9. The method as defined in claim 1 further comprising using an injection tool fastened detachably with said filling member to inject said pasty medicine into said holding portion via said injection tool.

10. The method as defined in claim 9, wherein said injection tool comprises a connection tube and a syringe formed of a barrel and a plunger, said connection tube being fastened detachably at one end with said injection port of said filling member, said connection tube further being fastened at other end with said barrel of said syringe; wherein said pasty medicine is injected into said holding portion of said filling member from said barrel by said plunger via said connection tube.

11. The method as defined in claim 10 further comprising using a sleeve to receive said connection tube and said implant in the sleeve prior to insertion of said implant into the bone, wherein said sutures protrude from said sleeve; inserting the sleeve into the bone; and withdrawing the sleeve from the bone.

12. The method as defined in claim 11 further comprising removing said sleeve from said connection tube, wherein said sleeve is made of a material having an elasticity and has a longitudinal slit, so that said sleeve can be removed from said connection tube by expanding said longitudinal slit.

13. The method as defined in claim 3, wherein said flexible wall of said implant is of a laminated multi-layered construction and each layer of said material contains said pores.

14. The method as defined in claim 13, wherein said pores in each layer are offset from the pores in the adjacent layer.

15. The method as defined in claim 1, wherein the other end of one or more sutures is fastened with a tissue by suturing.

* * * * *